(12) United States Patent
Fazlin

(10) Patent No.: US 10,962,471 B1
(45) Date of Patent: Mar. 30, 2021

(54) POINT OF CARE SYSTEM FOR QUANTIFYING COMPONENTS OF BLOOD

(71) Applicant: Fazal Fazlin, St. Petersburg, FL (US)

(72) Inventor: Fazal Fazlin, St. Petersburg, FL (US)

( * ) Notice: Subject to any disclaimer, the term of this patent is extended or adjusted under 35 U.S.C. 154(b) by 0 days.

(21) Appl. No.: 16/030,450

(22) Filed: Jul. 9, 2018

(51) Int. Cl.
  *G01N 21/27* (2006.01)
  *A61B 5/15* (2006.01)
  *A61B 10/00* (2006.01)
  *G01N 21/25* (2006.01)

(52) U.S. Cl.
  CPC ....... *G01N 21/27* (2013.01); *A61B 5/150022* (2013.01); *A61B 10/007* (2013.01); *A61B 10/0051* (2013.01); *A61B 10/0064* (2013.01); *G01N 21/255* (2013.01); *G01N 2201/06113* (2013.01)

(58) Field of Classification Search
  CPC ................. G01N 21/27; G01N 21/255; G01N 2201/06113; G01N 1/28; A61B 10/0051; A61B 10/0064; A61B 10/007; A61B 5/150022; A61B 5/157
  See application file for complete search history.

(56) References Cited

U.S. PATENT DOCUMENTS

| | | | | |
|---|---|---|---|---|
| 5,823,973 A * | 10/1998 | Racchini | ............ | A61B 5/14514 600/573 |
| 5,871,494 A * | 2/1999 | Simons | ............ | A61B 5/150022 604/137 |
| 6,614,522 B1 * | 9/2003 | Sopp | .................. | A61B 5/14514 356/244 |
| 7,137,957 B2 * | 11/2006 | Erickson | ............ | A61B 5/14514 600/573 |
| 2006/0023185 A1 * | 2/2006 | Hazelton | .................. | B08B 3/04 355/53 |
| 2019/0170633 A1 * | 6/2019 | Scherer | .................. | G01N 21/35 |
| 2019/0185799 A1 * | 6/2019 | Katou | .................... | B65D 77/06 |

* cited by examiner

*Primary Examiner* — Michael P LaPage
(74) *Attorney, Agent, or Firm* — Stephen Lewellyn; Lewellyn Law, PLLC

(57) ABSTRACT

A micro-cavity holder has an upper surface and a lower surface with a major recess in a generally cylindrical configuration. The major recess has an exterior periphery. The micro-cavity holder has a central aperture with a cylindrical central region and a lower region. A probe has a generally cylindrical configuration with an upper section and a lower section. The upper section has an exterior periphery removably received in the major recess to removably couple the probe and the micro-cavity holder. Cylindrical openings extend axially through the upper and lower sections of the probe and terminate above in a central recess. A transparent member is removably positioned in the central recess for receiving and supporting bodily fluids.

3 Claims, 3 Drawing Sheets

POINT OF CARE SYSTEM FOR QUANTIFYING COMPONENTS OF BLOOD

BACKGROUND OF THE INVENTION

Field of the Invention

The present invention relates to a point of care system for digitizing blood and more particularly pertains to a minimally invasive, rapid system for quantifying components of blood and other bodily fluids, such bodily fluids being sweat, urine, saliva, and the like. The system requiring a very small volume of fluid that can be obtained from a single needle prick. The single needle prick, and the digitizing of the blood, and the quantifying of the blood components being done in a safe, sanitary, convenient, and economical manner.

Description of the Prior Art

The use of blood analysis systems is known in the prior art. More specifically, known systems previously devised and utilized for the purpose of identifying, analyzing, and quantifying components of blood and other like bodily fluids are known to consist basically of familiar, expected, and obvious structural configurations, notwithstanding the myriad of designs encompassed by the crowded prior art which has been developed for the fulfillment of countless objectives and requirements.

While known devices fulfill their respective, particular objectives and requirements, they do not describe a minimally invasive point of care system for digitizing blood that rapidly quantifies components of the blood and requires only a very small volume of blood that can be obtained from a single needle prick where the single needle prick, and the digitizing of the blood, and the quantifying of the blood components being done in a safe, comfortable, and convenient, and economical manner.

In this respect, the point of care system for digitizing blood according to the present invention substantially departs from the conventional concepts and designs of the prior art, and in doing so provides an apparatus primarily developed for the purpose of rapidly digitizing very small volumes of blood for quantifying the components of the blood. The component quantifying and the rapid digitizing of the blood being done in a safe, comfortable, and convenient, and economical manner.

Therefore, it can be appreciated that there exists a continuing need for a new and improved point of care system for digitizing blood which can be used for rapidly digitizing very small volumes of blood for quantifying the components of the blood. The quantifying of the components and the rapid digitizing of the blood being done in a safe, comfortable, and convenient, and economical manner. In this regard, the present invention substantially fulfills this need.

SUMMARY OF THE INVENTION

In view of the disadvantages inherent in the known types of blood analysis systems of known designs and configurations now present in the prior art, the present invention provides an improved point of care system for digitizing blood. As such, the general purpose of the present invention, which will be described subsequently in greater detail, is to provide a new and improved point of care system for digitizing blood and method which has all the advantages of the prior art and none of the disadvantages.

To attain this, from a broad perspective, first provided is a micro-cavity holder having an upper surface and a lower surface with a major recess having a generally cylindrical configuration with an exterior periphery, a central aperture with a cylindrical central region and a lower region. A probe has an upper section and a lower section. The upper section has a generally cylindrical configuration and a generally cylindrical exterior periphery removably received in the major recess to removably couple the probe and the micro-cavity holder. Cylindrical openings extend axially through the upper and lower sections of the probe and through the micro-cavity holder. The cylindrical openings terminate above in a central recess. A transparent member is removably positioned in the central recess for receiving and supporting bodily fluids.

There has thus been outlined, rather broadly, the more important features of the invention in order that the detailed description thereof that follows may be better understood and in order that the present contribution to the art may be appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

It is to be understood that the inventions reference to blood is not limited and also includes other bodily fluids such as sweat, urine, saliva, and the like.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including such equivalent constructions insofar as they do not depart from the spirit and scope of the present invention.

It is therefore an object of the present invention to provide a new and improved point of care system for digitizing blood which has all the advantages of the prior blood analysis systems of known designs and configurations and none of the disadvantages.

It is another object of the present invention to provide a new and improved point of care system for digitizing blood which may be easily and efficiently manufactured and marketed.

It is a further object of the present invention to provide a new and improved point of care system for digitizing blood which is of durable and reliable constructions.

An even further object of the present invention is to provide a new and improved point of care system for digitizing blood which is susceptible of a low cost of manufacture with regard to both materials and labor, and which accordingly is then susceptible of low prices of sale, thereby making such point of care system for digitizing blood economically available.

Lastly, it is an object of the present invention to provide a point of care system for digitizing blood that rapidly quantifies the components of the blood and requires only a very small volume of fluid that can be obtained from a single needle prick where the single needle prick, and the digitizing of the blood, and the quantifying of the blood components being done in a safe, comfortable, and convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
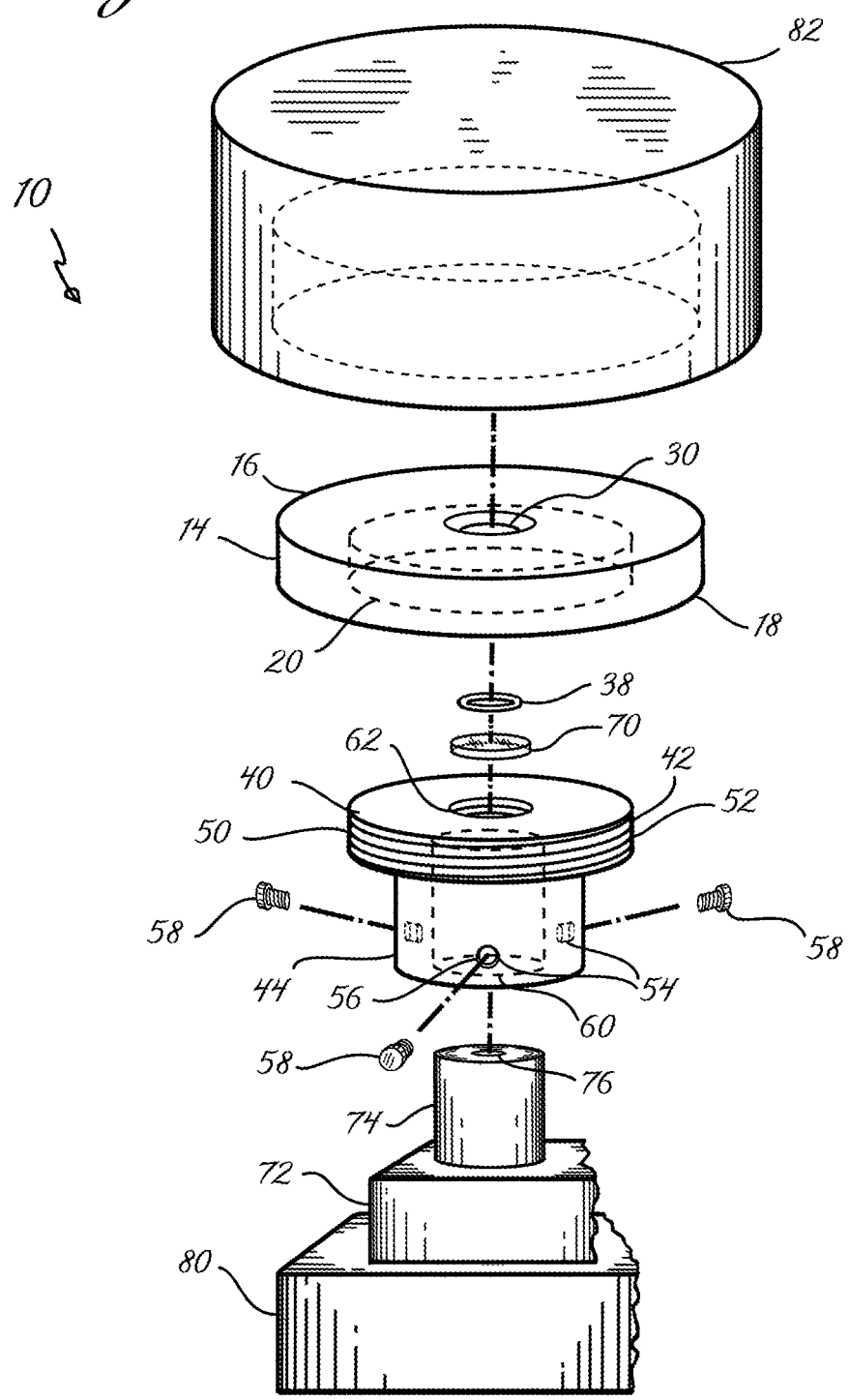
FIG. 1 is an exploded perspective illustration of a rapid point of care system for digitizing blood.
Figure 2A:
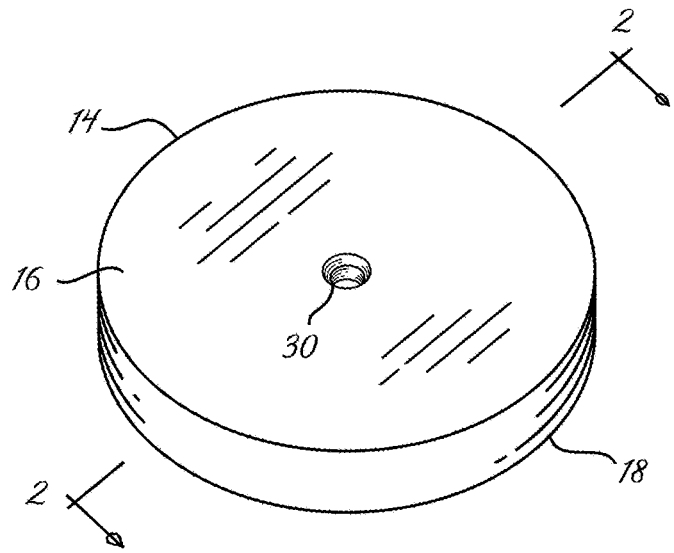
FIG. 2A is a top perspective illustration of the micro-cavity holder shown in FIG. 1.
Figure 2B:
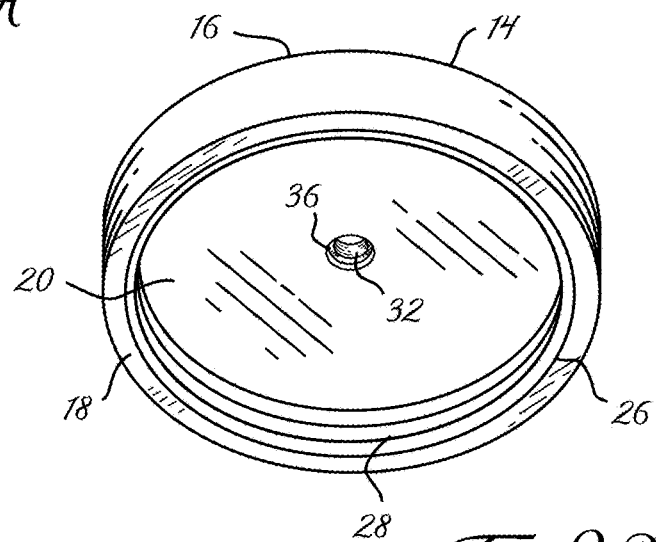
FIG. 2B is a bottom perspective illustration of the micro-cavity holder shown in FIG. 2.
Figure 2C:
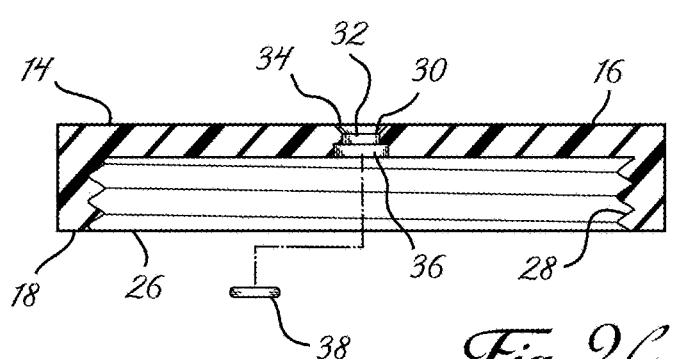
FIG. 2C is cross sectional view taken along line 2-2 of FIG. 2A.
Figure 3A:
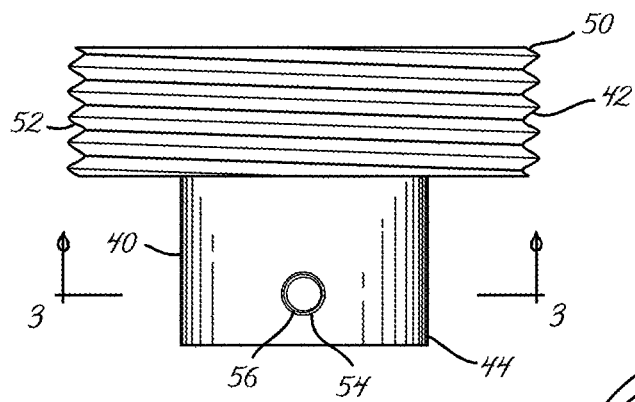
FIG. 3A is a top perspective illustration of the probe shown in FIG. 1.
Figure 3B:
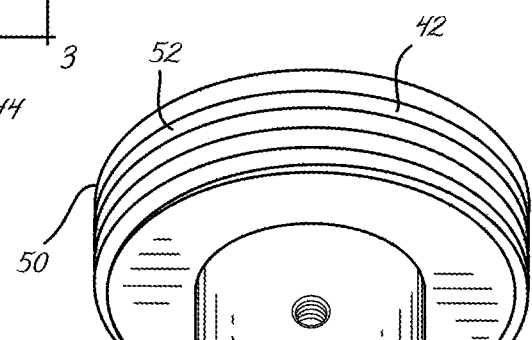
FIG. 3B is a bottom perspective illustration of the probe shown in FIG. 3B.
Figure 3C:
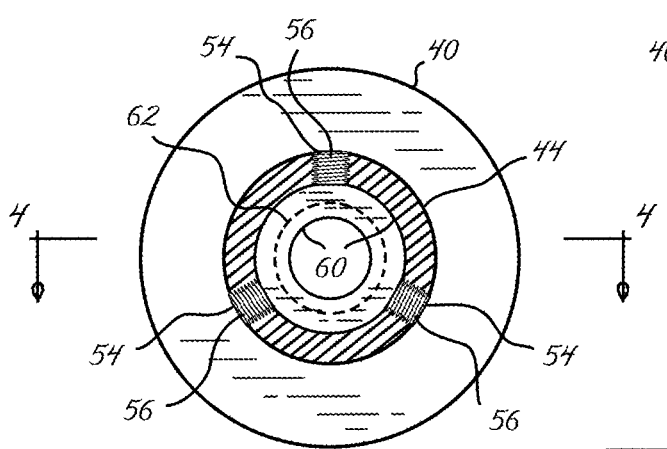
FIG. 3C is a cross sectional view taken along line 3-3 of FIG. 3A.
Figure 3D:
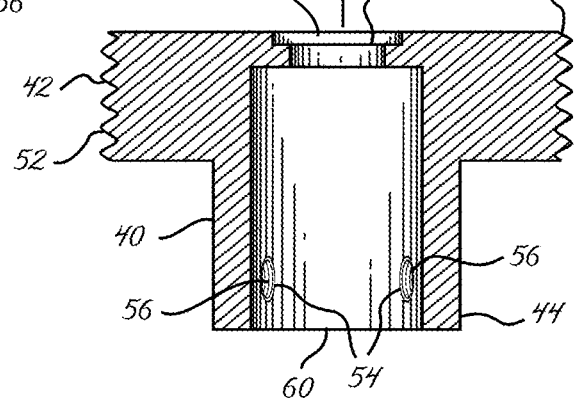
FIG. 3D is a cross sectional view taken along line 4-4 of FIG. 3C.

With reference now to the drawings, and in particular to FIG. 1 thereof, the preferred embodiment of the new and improved point of care system for digitizing blood embodying the principles and concepts of the present invention and generally designated by the reference, numeral 10 will be described.

The present invention, the point of care system for digitizing blood 10 is comprised of a plurality of components. Such components are individually configured and correlated with respect to each other so as to attain the desired objective. In their broadest context such include a micro-cavity holder, a probe, cylindrical openings, and a transparent member.

In the preferred embodiment of the point of care system for digitizing blood, designated by reference numeral 10, first provided is a micro-cavity holder 14 having a generally cylindrical configuration. The micro-cavity holder has an upper surface 16 in a circular configuration. The micro-cavity holder having a lower surface 18 with a major recess 20 in a generally cylindrical configuration with a depth and a diameter. The major recess has an exterior periphery 26 with female screw threads 28. The micro-cavity holder has a central aperture 30 adapted to function as a blood receiving well. The central aperture has a cylindrical central region 32, a frusto-conical upper region 34, and an enlarged lower region 36. An O-ring 38 is removably positioned in the enlarged lower region for providing a leak-proof mating surface. It should be noted that the O-ring can be replaced with other means of abating leakage from the enlarged lower region, such as adapting the configuration of the enlarged lower region with a circular ridge or a similar means of providing the leak abating. The central region of the central aperture having a diameter of 3 to 4.5 millimeters plus or minus 10 percent.

A probe 40 is next provided. The probe has an upper section 42 and a lower section 44. The upper section has a generally cylindrical configuration with a height essentially equal to the depth of the major recess and a diameter essentially equal to the diameter of the major recess. The upper section has a generally cylindrical exterior periphery 50 with male screw threads 52 removably received in the female screw threads of the major recess to removably couple the probe and the micro-cavity holder. It is also to be noted that the male screw threads and the female screw threads can be adapted and configured with an alternate means of removably coupling the probe and the micro-cavity holder such as a snap cap or a similar type of snap in fitting. The lower section has a generally cylindrical configuration with a height greater than the depth of the major recess and a diameter less than the diameter of the major recess. The lower section has three radial apertures 54 with female threads 56. The radial apertures are circumferentially spaced 120 degrees from one another. Three set screws 58 are provided. Each set screw is positioned in an associated threaded radial aperture. Cylindrical openings 60 extend axially through the upper and lower sections of the probe. The cylindrical openings terminate above in a central recess 62.

Next, a calcium fluoride glass 70 is provided. The calcium fluoride glass is removably positioned in the central recess for receiving and supporting blood in the well.

Further provided is a laser module 72. The laser module is positioned beneath the probe. The laser module is adapted to emit radiation upwardly through the cylindrical openings.

Provided next is a mounting component 74. The mounting component has a cylindrical configuration with an axial opening 76 extending upwardly from the laser module and into the lower section of the probe and secured to the probe by the set screws.

Next a spectrometer 80 is provided. The spectrometer is positioned beneath the laser module. The spectrometer is adapted to receive and analyze emissions emitted upwardly from the laser module to the blood then reflected downwardly to the spectrometer.

Lastly provided is a cover 82. The cover is removably positioned over the micro-cavity holder and the probe and the mounting component. The cover is fabricated of an opaque material and adapted to shield the system from ambient light during operation and use. It is to be noted that the cover can be alternately configured in such a way that the cover is removably positioned over the micro-cavity holder only and not positioned over the probe and the mounting component. Additionally, the cover can be alternatively configured to be removably positioned over the micro-cavity holder and the probe and not positioned over the mounting component.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A point of care system for digitizing bodily fluids, the system comprising:
    a micro-cavity holder having an upper surface and a lower surface with a major recess in a cylindrical configuration, the major recess having an exterior periphery, the micro-cavity holder having a central aperture with a cylindrical central region and a lower region;
    a probe having an upper section and a lower section, the supper section having a cylindrical configuration, the upper section having a cylindrical exterior periphery removably received in the major recess to removably couple the probe and the micro-cavity holder;
    cylindrical openings extending axially through the upper and lower sections of the probe, the cylindrical openings terminating above in a central recess, a transparent member removably positioned in the central recess for receiving and supporting bodily fluids;
    wherein the lower section has a plurality of apertures with female threads, a plurality of set screws, one set screw positioned in an associated radial aperture;
    a laser module positioned beneath the probe, the laser module adapted to emit radiation upwardly through the cylindrical openings;
    a mounting component in a cylindrical configuration with an axial opening extending upwardly from the laser module and into the lower section of the probed and secured by the set screws; and
    a spectrometer positioned beneath the laser module, the spectrometer adapted to receive and analyze emissions emitted upwardly from the laser module to blood disposed in the micro cavity-holder and reflected downwardly to the spectrometer.

2. The system as set forth in claim 1 and further including:
    a cover removably positioned over the micro-cavity holder and the probe, the cover adapted to shield the system from light during operation and use.

3. A minimally invasive, rapid, point of care system for digitizing blood by quantifying components of the blood, the system requiring a very small volume of blood that can be obtained from a single needle prick, the system comprising, in combination:
    a micro-cavity holder in a cylindrical configuration, the micro-cavity holder having an upper surface in a circular configuration, the micro-cavity holder having a lower surface with a major recess in a cylindrical configuration with a depth and a diameter, the major recess having an exterior periphery with female screw threads, the micro-cavity holder having a central aperture adapted to function as a blood receiving well, the central aperture having a cylindrical central region and a frusto-conical upper region and an enlarged lower region, an O-ring removably positioned in the enlarged lower region, the central region of the central aperture having a diameter of 3 to 4.5 millimeters plus or minus 10 percent;
    a probe having an upper section and a lower section, the upper section having a cylindrical configuration with a height about equal to the depth of the major recess and a diameter about equal to the diameter of the major recess, the upper section having a generally cylindrical exterior periphery with male screw threads removably received in the female screw threads of the major recess to removably couple the probe and the micro-cavity holder;
    the lower section having a cylindrical configuration with a height greater than the depth of the major recess and a diameter less than the diameter of the major recess, the lower section having three radial apertures with female threads circumferentially spaced each 120 degrees, three set screws, each set screw positioned in an associated threaded radial aperture, cylindrical openings extending axially through the upper and lower sections of the probe, the cylindrical openings terminating above in a central recess;
    a calcium fluoride glass removably positioned in the central recess for receiving and supporting blood in the well;
    a laser module positioned beneath the probe, the laser module adapted to emit radiation upwardly through the openings;
    a mounting component in a cylindrical configuration with an axial opening extending upwardly from the laser module and into the lower section of the probe and secured to the probe by the set screws;
    a spectrometer positioned beneath the laser module, the spectrometer adapted to receive and analyze emissions emitted upwardly from the laser module to the blood then reflected downwardly to the spectrometer;
    a cover removably positioned over the micro-cavity holder and the probe, the cover adapted to shield the system from ambient light during operation and use.

\* \* \* \* \*